United States Patent [19]

Tochacek et al.

[11] Patent Number: 5,368,668
[45] Date of Patent: Nov. 29, 1994

[54] STITCHBONDED ABSORBENT ARTICLES AND METHOD OF MAKING SAME

[75] Inventors: Miroslav Tochacek, Woodbury; Donald M. Courteau, Maplewood, both of Minn.

[73] Assignee: Minnesota Mining and Manufacturing Company, St. Paul, Minn.

[21] Appl. No.: 204,667

[22] Filed: Mar. 2, 1994

Related U.S. Application Data

[62] Division of Ser. No. 879,876, May 7, 1992, Pat. No. 5,308,673.

[51] Int. Cl.⁵ .............................................. B32B 7/08
[52] U.S. Cl. .................................... 156/93; 66/83; 66/192; 156/91; 156/148; 156/308.2; 156/308.4; 156/309.6
[58] Field of Search ............................... 156/91–93, 156/148, 308.2, 308.4, 309.6; 66/83, 192, 174

[56] References Cited

U.S. PATENT DOCUMENTS

| | | | |
|---|---|---|---|
| 3,030,786 | 4/1962 | Mauersberger | 66/84 |
| 3,279,221 | 10/1966 | Glicksmann | 66/192 |
| 3,717,150 | 2/1973 | Schwartz | 128/284 |
| 3,837,943 | 9/1974 | Ploch et al. | |
| 3,881,490 | 5/1975 | Whitehead et al. | 128/287 |
| 4,100,324 | 7/1978 | Anderson et al. | 428/288 |
| 4,675,226 | 6/1987 | Ott | 428/102 |
| 4,704,321 | 11/1987 | Zafiroglu | 428/230 |
| 4,773,238 | 9/1988 | Zafiroglu | 66/192 |
| 4,876,128 | 10/1989 | Zafiroglu | 428/102 |
| 5,041,255 | 8/1991 | Zafiroglu | 264/288 |

FOREIGN PATENT DOCUMENTS

| | | |
|---|---|---|
| 162277 | 11/1976 | Czechoslovakia . |
| 193700 | 1/1979 | Czechoslovakia . |
| 2227318 | 8/1973 | Germany . |
| 2209352A | 1/1976 | United Kingdom . |

OTHER PUBLICATIONS

Julius C. Parrella, "Nonwoven Technology and Wipers", presented at INDA-TEC 1989.

*Primary Examiner*—James J. Bell
*Attorney, Agent, or Firm*—Gary L. Griswold; Walter N. Kirn; Jeffrey L. Wendt

[57] ABSTRACT

A stitchbonded absorbent article and method of making same are presented. The article exhibits good hand, repeated washing durability, and absorbency. The article includes first and second layers which are mechanically held together by stitches of yarn, at a stitch density ranging from about 15 to about 35 st/10 cm, and stitch gauge ranging from about 10 to about 40, using a stitching yarn comprising at least two compositionally different fibers having different heat stability being at least partially melt-bonded together at points of mutual contact, the yarn being melt-bonded at least partially to outer surfaces of the article.

4 Claims, 3 Drawing Sheets

STITCHBONDED ABSORBENT ARTICLES AND METHOD OF MAKING SAME

This is a division of application Ser. No. 07/879,876 filed May 7, 1992, now U.S. Pat. No. 5,308,673.

FIELD OF THE INVENTION

This invention pertains to stitchbonded, durable, absorbent articles made using a stitching yarn having fibers of differing heat stabilities, and to methods of producing such articles.

BACKGROUND ART

Parella, J. C., "Nonwoven Technology and Wipers", paper presented at INDA-TEC 1989, presents a perceptive account of the nonwoven industry. Specifically, Parella describes and compares the four primary techniques that commercial manufacturers have focused on for producing wipes. In order of commercialization they are:

dry staple (carded, air laid, saturation or spray bonded webs made from textile fibers);

air-lay (fabric made by air laying and bonding cellulosic or synthetic pulp fibers);

melt blown (webs formed by in-line melt spinning of very fine fibers); and spunlace (fabrics produced by hydraulic entangling of fibers).

Parella compares these primarily using the "alphabet" of consumer driven requirements for wipes: "A" for absorbency; "B" for bulk density; "C" for consistency; "D" for durability; and "P" for price.

Dry staple nonwoven wipes were acceptable in terms of A and D, but P was a premium over 100% cellulosic paper wipes. Wipes made using the air-lay process generally met consumer needs for A, B, C, and P but fell short on improving D over already available dry staple nonwoven wipes. Despite this, product acceptance was almost immediate in industrial and consumer sectors. Fabrics made from melt blown fibers exhibited outstanding oil absorbency, and aqueous absorbency was acceptable. Adsorption or entrapment is the method of absorbency employed rather than absorption into the fiber or cellulose as in the use of the dry staple or air laying techniques. B, C, D, and P were adequate but not dramatically different from prior wipes. Spunlaced fabrics were said to be "the most complete nonwoven wiper seen to date" in terms of A, B, C, and D, and P was "within the range of acceptance given the performance characteristics."

Whitehead et al. (U.S. Pat. No. 3,881,490), at column 4, line 63, through column 5, line 68) gives a respectable rendition of the air-lay technique of fabricating nonwoven wipes. However, Anderson et al. (U.S. Pat. No. 4,100,324) describes one apparent disadvantage of air lay wood pulp fiber webs, that they exhibit reduced absorbent capacity and rate (as compared to mechanically entangled webs of wood and synthetic pulp fibers) due to the adhesive used to contain the wood pulp fibers.

Stitchbonding, as a method of bonding two fabrics together to form a durable, absorbent wipe, has apparently not received the amount of attention of the wipes industry as have the above mentioned techniques. Schwartz, in U.S. Pat. No. 3,717,150, describes an absorbent stretchable diaper comprising a layer of hydrophilic material, at least one layer of hydrophobic material, stitched together with substantially non-shrinkable yarn. The hydrophilic and hydrophobic layers are maintained in contact with each other by a series of interconnected loop chains of the yarn knitted through the layers to encase the layers in a warp knitted fabric of the yarn. After being encased in the yarn the edges of the fabric are preferably covered by a border which is stitched into place to prevent the yarn from unraveling. The preferred stitch density ranges from 28 st/10 cm to about 55 st/10 cm. Schwartz notes that a greater number of stitches per unit length increases the durability of the construction but decreases its absorbency, and that when a lower stitch density is used, fibers are typically longer (typically about 9 cm) to minimize fiber loss during laundering. No mention is made of the use yarns of differing heat stability.

Two Czechoslovakian patents, 162277 (issued Nov. 15, 1976) and 193700 (published Jan. 31, 1979), relate to stitchbonded materials. The '277 patent is drawn toward a nonwoven fabric, suitable for use as a wipe, comprising base loose fibers of natural or chemical fibers having on at least one side thereof attached a layer of lintless, bonded nonwoven fabric made by the wet laid process. No mention is made of web adhesives used in the wet laid material except that "chemical binders" are used to bond the fibers together. All layers are mechanically connected together by one or more stitching yarns, none of which is disclosed as having melting point below 175° C.

The '700 Czechoslovakian patent describes a stitchbonded article, the stitching yarn containing at least two yarns of differing heat stability. The products are primarily described as being useful as an underlay fabric for pile loop stitchbonded or tufted textiles, or as an inlay scrim for needlepunched fabric. The only Example pertaining to a wipe is Example 1, which describes a single batt of cotton/viscose blend weighing 350 g/m$^2$ stitched through using two yarns: a 120 denier polyamide yarn (melting point about 220° C.), and a 100 denier polypropylene yarn (melting point 160°–170° C.). Both yarns are threaded through the same lapping guide in threading order 1 to 1, in the chain/plain structure offset mode, with a stitch density of 50 st/10 cm. The stitched material was subjected to heat treatment via air drum dryers at a temperature of 175° C. and speed of 20 m/min with following cooldown. The finished article as it appears from the technical back side is illustrated in a schematic perspective view in FIG. 1A, showing the article 10 comprised of the cotton/viscose batt 12, plain stitch 14 of polyamide yarn, and chain stitch 16 of polypropylene yarn. FIG. 1B is a schematic representation of the stitching pattern used, and also how the lapping bars or guides are threaded. No criticality is given to the stitch density, stitch gauge (as defined herein), or fibrous web composition as they relate to rate and absolute amount of water absorbency or durability of these wipes.

Ott (U.S. Pat. No. 4,675,226), describes a stitchbonded composite wiper having a middle layer of cellulose natural fibers and outer layers of either continuous filament thermoplastic fibers, meltblown thermoplastic microfibers or rayon fibers. The layers are laminated into a composite by chain stitchbonding using stitching yarn of either polyester, cotton, rayon, nylon or a blend. The stitch density (number of stitches per 10 cm in machine direction) is given as ranging from 20 to 100 st/10, with 30 st/10 cm preferred. The stitch gauge is given as ranging from 3.5 to 22 lines per inch (claim 1), or 14 to 87 gauge (needles per 10 cm), with 55 gauge (or 14 wales/in.) being preferred. No suggestion is provided for using stitching yarns of differing heat stabilities, or of the type of adhesive preferred in the cellulose fiber layers.

The manner of producing stitchbonded materials is performed by stitchbonding machines, such as that known under the trade designation "Maliwatt" as described in U.S. Pat. Nos. 2,890,579; 3,030,786; and 3,279,221. Equivalent machines, such as that known under the trade designation "Arachne" can be used for preparing the stitchbonded materials which are precursors to the articles of the present invention.

A series of patents by Zafiroglu describes nonwoven fabrics which are multi-needle stitched with an elastic yarn (U.S. Pat. Nos. 4,704,321; 4,773,238; 4,876,128; and 5,041,255).

SUMMARY OF THE INVENTION

In accordance with the present invention, a stitchbonded absorbent article is presented comprising a nonwoven batt consisting essentially of cellulosic pulp fibers bonded together by an adhesive binder. The bonding of the fibers may be by thermoplastic powder bonding, thermoplastic fibers, or by spray bonding. Preferred is spray bonded batts, using acrylic latex-based adhesive binders. The batt has a basis weight of at least about 95 g/m$^2$ (gsm) per ply. The batt is stitchbonded, using a plain or tricot stitch, with a stitching yarn comprising two compositionally different fibers having different heat stability. In the final form of the absorbent articles of the invention the two fibers are at least partially melt-bonded together after stitching, and are also melt-bonded to at least a portion of the external surfaces of the articles after stitching.

In one class of preferred embodiments, a second layer is stitchbonded to the first layer. The second layer comprises materials selected from the group consisting of
  i) a second nonwoven batt consisting essentially of cellulosic pulp fibers bonded together by an adhesive binder, wherein the second batt may be the same or different from the first batt; and
  ii) a woven, nonwoven, or knitted layer of materials selected from the group consisting of viscose rayon, cotton, non-polyolefin synthetic fibers, and mixtures thereof.

The first and second (or more) layers are mechanically held together by stitches of yarn, preferably a plain or tricot stitch. A stitch density (number of stitches in the machine direction per 10 cm) ranging from about 15 to about 35 st/10 cm, and stitch gauge (number of stitch wales per 10 cm) ranging from about 10 to about 40, have been found to afford the articles with surprisingly good water absorbency properties (rate and absolute) and durability when used in conjunction with the adhesive bonded cellulosic pulp fiber batts.

It was unexpected that the increase in durability of the articles of the invention could be obtained by stitchbonding with only a slight decrease in water absorbency properties compared with a non-stitchbonded article of otherwise similar construction. The "hand" properties, flexibility, and drapability are also not substantially decreased over non-stitchbonded articles of similar construction, and an essentially disposable item is rendered into a multi-use item, reducing waste disposal problems. The attractiveness of articles of the invention can be modified by changing the colors of the stitching yarns and/or the layers used to make the articles.

A stitching yarn comprising at least two compositionally different fibers, and thus of different heat stability, is used. The two fibers are melt-bonded to each other along at least a portion of their contact area, and at least a portion of the yarn is in turn melt-bonded to the outer surfaces of the articles.

As used herein "cellulosic pulp fibers" means cellulosic fibers, such as wood pulp fibers, having a length ranging from about 3 to about 5 mm, and diameter ranging from about 15 to about 40 micrometers (denier ranging from about 1 to about 5 dtex). Thus, these fibers are distinguished from staple or textile fibers (which generally have between about 2 and 9 cm) and continuous filaments. "Consisting essentially of nonwoven cellulosic pulp fibers" means that the batt contains zero or a de minimis amount of fibers which do not meet the definition of "pulp fibers".

One particularly preferred class of articles of the invention are those wherein the second layer comprises a second batt of nonwoven cellulosic pulp fibers bonded together by an adhesive binder.

Also preferred absorbent articles within the invention are those wherein the second layer comprises viscose rayon fibers. Particularly preferred articles of this class are those wherein the article includes a third layer similar to the second layer, the second and third layers forming a sandwich around the first layer.

Another aspect of the invention is a method of manufacturing a stitchbonded absorbent article of the invention as herein described, wherein the method comprises as a first step forming a stitchbonded material having a stitch density ranging from about 15 to about 35 st/10 cm, and stitch gauge ranging from about 14 to about 40, using a yarn comprising first and second compositionally different fibers having different heat stability. Thereafter the stitchbonded material is heated for a time and at a temperature sufficient to partially melt the lower melting temperature fibers but insufficient to melt the higher melting temperature fiber, thereby melt-bonding at least a portion of the first and second fibers together and melt-bonding at least a portion of the first lower melting fiber to the outer surfaces of the article.

Further features and advantages of the invention will be described in reference to the detailed description and examples which follow.

DESCRIPTION OF PREFERRED EMBODIMENTS

Figure 1A:
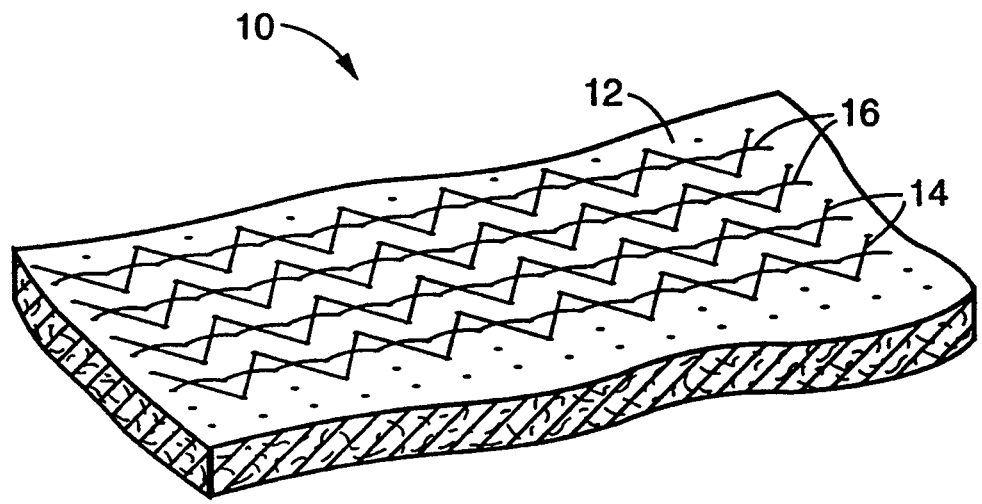
FIG. 1A is a perspective schematic view of the article of Czech patent 193700 Example 1, showing the plain/-chain combination stitch.
Figure 1B:
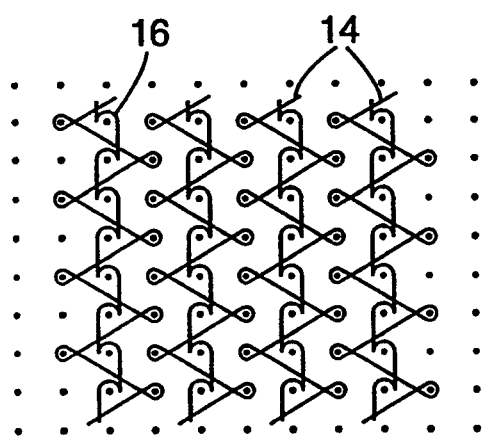
FIG. 1B is a schematic representation of the stitch structure of the article illustrated in FIG. 1A.

As previously noted, in all absorbent article embodiments in accordance with the invention, the first (or only) layer of material comprises a first batt of nonwoven cellulosic pulp fibers bonded together by an adhesive binder, the first batt having a basis weight of at least about 95 grams/m$^2$ (gsm) per ply.

It should thus be noted that all absorbent articles of the invention are water absorbent and very durable, and yet are inexpensive to produce. Particularly, if the absorbent articles of the invention are made from 100% cellulosic pulp fibers, the articles of the invention are low in cost compared with articles based on synthetic wood pulp fibers. Articles which include a second or third layers of 100% viscose rayon or cotton are similarly relatively inexpensive to produce, thus reducing cost to the ultimate user.

The adhesive binder of the first and, if used, second batts of cellulosic pulp fiber may comprise any of the commonly used adhesive binders known in the art. Typically and preferably the adhesive binder comprises a copolymer of ethylene and vinyl acetate, wherein the vinyl acetate is present at about 10 to about 20 weight percent of the copolymer. Cellulosic wood pulp batts having this adhesive and found useful in the invention include those known under the trade designation "Airtex", from James River Corporation, especially product numbers 395 and 399. The 399 version is more absorbent but less strong than the 395 version. Although the composition of these batts is proprietary, it is believed the adhesive generally comprises from about 2 to about 20 weight percent of the adhesive bonded cellulosic pulp fiber batts.

The second layer, or more layers if preferred depending on the end use, comprises materials selected from the group consisting of
i) a second batt of nonwoven cellulosic pulp fibers bonded together by an adhesive, the second batt being the same or different than the first batt, and
ii) a woven, nonwoven, or knitted layer of materials selected from the group consisting of viscose rayon, cotton, non-polyolefin synthetic fibers, and mixtures thereof.

If the second layer is viscose rayon, this layer is preferably nonwoven, more preferably spunlaced nonwoven. Suitable spunlaced 100% viscose rayon layers are available from various commercial sources. One spunlaced 100% viscose rayon layer found useful for the purposes of this invention is that sold under the trade designation "Brand 6411 Apertured" from Scott Paper Company.

The first and second layers are stitchbonded using a stitch density (stitches per 10 cm in machine direction) ranging from about 15 to about 35 st/10 cm, more preferably ranging from about 20 to about 30 st/10 cm.

The stitch gauge (number of vertical lines of stitches (wales) per 10 cm in cross direction) ranges from about 10 to about 40, preferably from about 13 to about 28 gauge, more preferably about 20 gauge.

Stitching densities and gauges outside of these ranges, especially when used with embodiments having no second viscose rayon layer, have been found inadequate in meeting the acceptable durability, absorbency, and consistency that users have come to demand. For example, stitchbonded articles having stitch density greater than about 35 st/10 cm were found to have unacceptable water absorbency rate and total water absorbency values. Stitchbonded articles of the invention having stitch density less than about 15 st/10 cm were found to lack acceptable durability. To be acceptable and thus within this invention, stitchbonded article durability (measured as peak load in a tensile test) should be greater than or equal to about 4.5 kg for one and two layer articles, and greater than or equal to 9 kg for three layer articles, as measured according to American Society of Testing Materials (ASTM) D-1682-64 (reapproved 1975). This test is described in the Examples. Acceptable water absorbency is determined by a "drip" test, wherein the article is soaked in water, allowed to drip for 60 seconds, then oven dried, after which the dried and 60 second drip weights are compared. The results are given as a percentage of the oven dried weight. To be acceptable, the stitchbonded articles of the invention should exhibit a 60 second drip value of at least about 400%. This test is also described in the Examples.

Articles of the invention having stitch gauge of above about 40 exhibit decreased water absorbency due to higher degree of compression of the absorbent cellulosic pulp fiber layer(s). Thus, stitching gauges higher than about 40 are not advantageous for stitching prebonded cellulosic pulp based nonwoven layers due to excessive perforation by the stitching needles, resulting in diminished original tensile strength and integrity of the absorbent cellulosic pulp layer(s).

As mentioned previously, a critical aspect of the invention is the use of a yarn comprising at least two compositionally different types of fibers having different heat stability which can be at least partially melt-bonded together. The yarn is also capable of melt-bonding to at least a portion of the article outer surfaces.

Preferably, the yarn comprises a first fiber having a melting temperature below that of the cellulosic pulp fiber but no greater than about 175° C., and a second fiber having a melting temperature of at least about 200° C., more preferably at least about 240° C.

The portion of the yarn having a melting temperature below that of the cellulosic pulp fiber but no greater than about 175° C. may be polyolefins selected from the group consisting of branched polyethylene, linear polyethylene, polypropylene, and mixtures thereof. Particularly preferred is polypropylene, which has a melting temperature range of about 160°–170° C. The denier of these fibers should be such as to allow sufficient bonding between the higher melting temperature fibers of the yarn and the cellulosic or viscose rayon layer outer surface. Otherwise, the denier of these fibers is not critical, and may range from about 40 to about 200 denier, more preferably from about 70 to about 100 denier. Fiber deniers lower than about 40 are difficult to melt-bond simply because of there is less mass of the fiber.

The second fiber having a melting temperature of at least about 200° C. may be chosen from polyester (polyethylene terephthalate melts at about 248° C.), alpha-cellulose (cotton) and rayon (decomposes after long exposure to temperatures of about 225° C.), protein, acetate, fluorocarbon, polyacrylonitrile, polyamide (the various nylons melt at about 220° C.), and mixtures thereof.

Particularly preferred as the second fiber is polyethylene terephthalate (PET) polyester. These fibers have the advantage of drawing water toward the absorbent layer in the case where viscose rayon is used as second and third cover layers. The interconnected network of the PET stitches through the layers of the articles of the invention increases the strength of the articles, and provides the durability demanded by users for repeated washing.

The denier of the second fibers is also not critical, and may range from about 10 to about 400 denier, more preferably from about 120 to about 180 denier. Fibers having lower denier than about 70 are presently not preferred as they may be too weak in tensile strength; however, should fibers having denier less than 70 become available which provide the requisite strength to the articles of the invention, these may also be used. Fiber deniers above about 400 are more expensive and generally not required for increasing the durability of the articles of the invention beyond the point where the user would normally dispose of the article. Larger denier fibers are also more expensive and may not biodegrade in an acceptable time.

Figure 2:
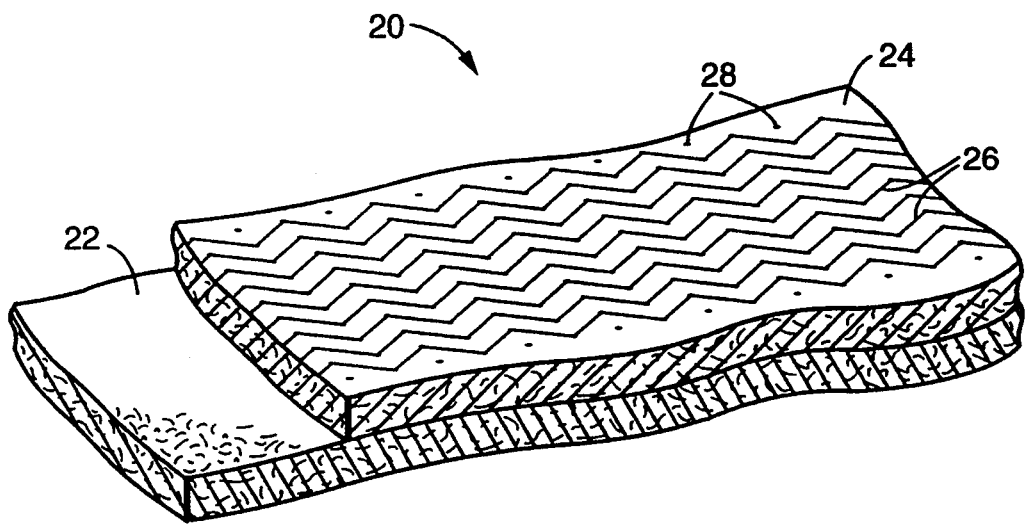
FIGS. 2–5 show perspective schematic views of absorbent articles within the invention.

One preferred absorbent article embodiment 20 of the invention is illustrated in perspective in FIG. 2. In this embodiment, a first layer 22 of a batt of adhesive bonded cellulosic pulp fibers (such as those sold under the trade designations "Airtex 395" and "Airtex 399") is stitchbonded to a second layer 24 of a batt of adhesive bonded nonwoven cellulosic pulp fibers (such as those known under the trade designations "Airtex 395" and "Airtex 399"). The "technical backside" of article 20 is shown on top, showing the preferred "plain" stitch pattern of stitching yarn 26 used in the articles of the invention. A "tricot" stitch may also be used. Holes 28 are shown slightly exaggerated in size to emphasize the point where individual needles have penetrated the layers. Alternately, either one of or both layers 22 and 24 may be a nonwoven mixture of rayon/non-polyolefin synthetic fibers, or, more preferably, 100% cellulosic fibers. Higher than about 30 weight percent non-polyolefin synthetic fibers are not preferred due the decrease in water absorbency of the articles of the invention. Suitable non-polyolefin synthetic fibers include polyester, acrylic, polyamide, and the like.

Figure 3:
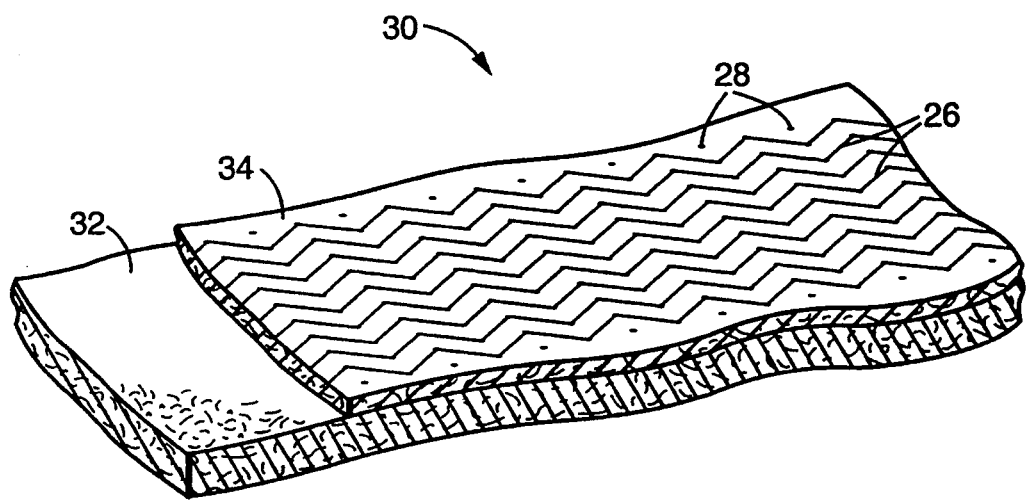

Another preferred embodiment 30 of the absorbent article of the invention is illustrated in FIG. 3, also as a perspective schematic. In this embodiment, the first layer 32 is the same as the first layer 22 of embodiment 20 shown in FIG. 2; however, the second layer 34 in this embodiment is constructed from woven, nonwoven, or knitted viscose rayon fibers. Layer 34 is preferably spunlaced viscose rayon fibers. Alternatively, layer 34 could be cotton or a mixture of cotton and viscose rayon fibers.

Figure 4:
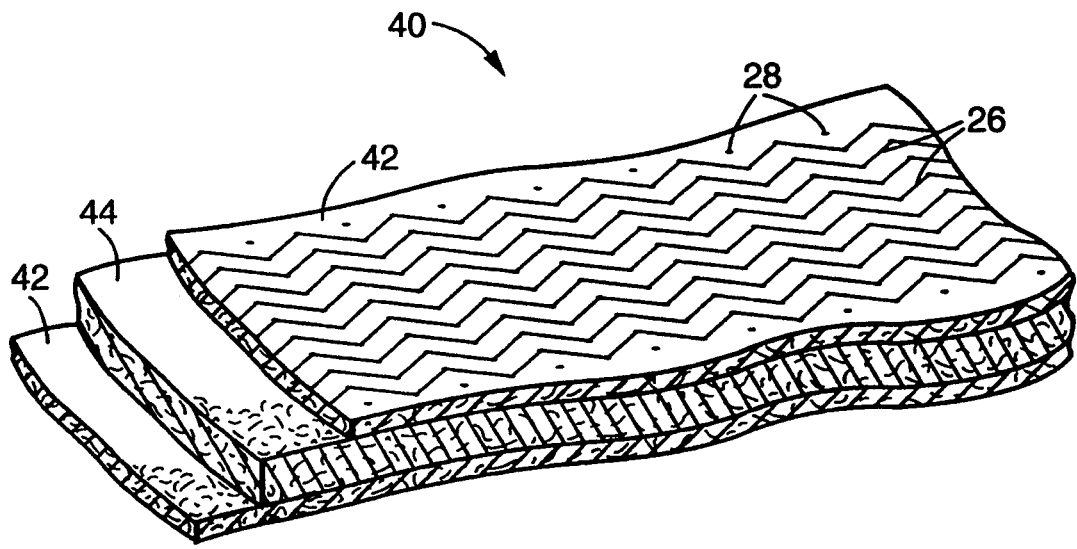

FIG. 4 illustrates another embodiment 40, similar to the embodiment illustrated in FIG. 3, except that embodiment 40 includes three layers stitchbonded together. Layer 44 comprises an adhesive bonded cellulosic pulp fiber batt or combination rayon/polyolefin batt as above described in reference to FIG. 2, while layers 42 comprise woven, nonwoven, or knitted viscose rayon, preferably spunlaced viscose rayon. Stitching yarn 26 and holes 28 in FIGS. 3 and 4 are the same as in the embodiments illustrated in FIGS. 2 and 3.

Figure 5:
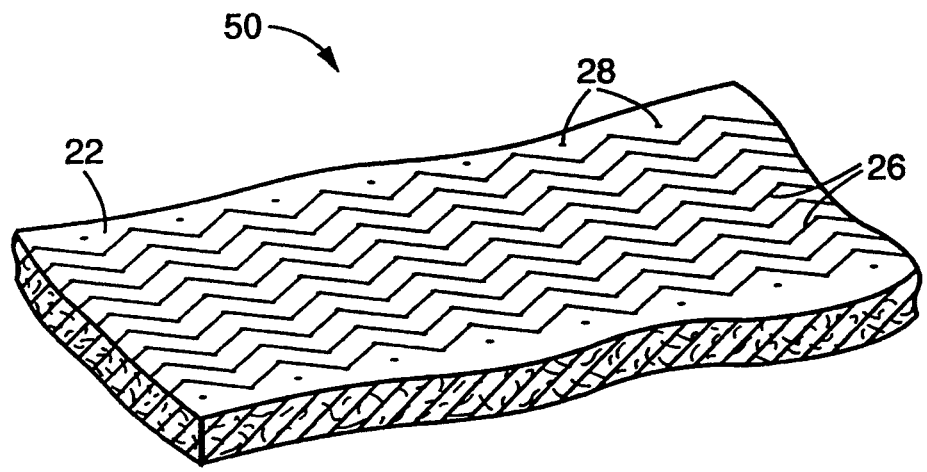

FIG. 5 illustrates embodiment 50, again in a perspective schematic view, a single layer of cellulosic pulp fibers and binder 22 stitchbonded through using a plain stitch of two component yarn 26, as described in reference to the previous embodiments.

The method of manufacturing stitchbonded absorbent articles of the invention comprises first forming a stitchbonded fabric having a stitch density ranging from about 15 to about 35 st/10 cm, and stitch gauge ranging from about 10 to about 40 wales/10 cm, using a plain or tricot stitch. Stitchbonding machines known under the trade designations "Maliwatt" and "Arachne" are adequate for these purposes.

A yarn as above described comprising first and second fibers of different heat stability, preferably 80 denier polypropylene and 150 denier polyester, is used. Thereafter, the stitchbonded material is passed through a heated space for a time and at a temperature sufficient to melt the fibers having lower melting temperature but insufficient to melt the fibers having higher melting temperatures. This causes melt-bonding of at least a portion of the lower melting fibers to the higher melting fibers and melt-bonding of at least a portion of the low melting fibers to the outer surfaces of the cellulosic pulp and viscose rayon layers, depending on the layers used. The stitchbonded, melt-bonded article is then cooled and is ready to be cut into individual absorbent articles of the invention.

One method of heating the stitchbonded article to cause melt bonding to occur is by contacting the stitchbonded fabric to a series of perforated or screen drums which are designed to have heated gas passed therethrough (air of relative humidity below about 70% being the preferred gas). The stitchbonded fabric is typically and preferably passed on the top side of one drum and the bottom side of the next succeeding drum in known fashion. Heated air or other gas is drawn through the stitchbonded fabric and the perforations or screen of the drums by reducing the pressure on the inside of the drums in a manner which maintains the loft of the layer but is just sufficient to keep the layer in contact with the drum. For this method, the time sufficient to cause the melt bonding to occur varies with the temperature of the heated air. Typically, if the temperature ranges from about 200° to about 210° C., the time ranges from about 15 to about 25 seconds. It is important to keep the time required at a minimum as the nonwoven cellulosic pulp materials may begin to oxidize slightly (turn mildly yellow) if time at temperature is too long.

Other methods of heating the stitchbonded fabric, may be used, such as passing the stitchbonded fabric through an open, heated passage having air circulation without drums, as for example in a tenter frame dryer. Tenter frame dryers are well known in the art.

The articles of the invention will now be described with reference to the following examples and test methods, wherein all percentages and parts are by weight unless otherwise specified.

TEST METHODS

Test Method I

Total Absorption With Drip

Scope:

The purpose of the this test was to measure the amount of water that stitchbonded absorbent articles of the invention could absorb (as a percentage of the article's dry weight, M) and how much water was retained under a gravity load.

Equipment:

1. A large container (beaker) that was capable holding the test samples and an excess of deionized water.
2. Deionized (D.I.) water.
3. Analytical balance accurate to ±0.01 gm.
4. A flat glass plate (black glass is preferable) with a 10.2 cm × 20.4 cm rectangular section (test area) marked off. There was adequate clearance of the test area from the edge of the glass plate (greater than 7.6 cm).
5. A negative clearance nip roller with rubber rolls of durometer 25T/27B rating and a negative clearance of 0.35 cm.
6. Stopwatch accurate to ±0.5 sec.
7. A controlled environment of 18°–24° C. and 45–55 percent relative humidity (RH).

In addition, a weighing tray large enough to hold the example absorbent articles, a flat perforated steel screen large enough to fully support the samples, tweezers, and an oven to dry the wet example absorbent articles were used.

Example size:

15.2 cm×20.3 cm stitchbonded absorbent articles of the invention and control Examples that have been preconditioned (see below).

Preconditioning of Example Absorbent Articles:

1. Absorbent articles were immersed in 15°-25° C. tap water and allowed the to soak for at least 1 minute. The articles were then squeezed to remove entrapped air bubbles, and subsequently wrung using the nip roller to remove excess water. This procedure was repeated for a total of 8 times for each absorbent article tested.

2. The articles from step 1 were immersed individually in 15°-25° C. deionized water, and allowed the to soak for at least i minute. The articles were then squeezed to remove entrapped air bubbles, and subsequently wrung using the nip roller to remove excess water. This procedure was repeated for a total of 2 times for each absorbent article tested.

Procedure for Absorption With Drip:

1. The preconditioned example absorbent articles were immersed in deionized water using the large container, squeezing to remove air, for at least 5 minutes or until they appeared to be totally saturated.

2. The immersed example absorbent articles were removed from the large container by grabbing at one corner with the tweezers. The example absorbent articles were allowed to drip from the opposite corner for 60 secs, and the time allotted for the drip recorded.

3. The example absorbent articles were placed onto the balance and the weight recorded as M1 to the nearest 0.01 gm.

4. Each example absorbent article was wrung using the nip roller by first running the article through the roller and then folding it into quarters and wringing the article again.

5. Each example absorbent article was reimmersed in the deionized water for at least 30 seconds.

6. Steps 2-5 were repeated for a total of 3 times per sample, recording each result.

7. The test was repeated for two example absorbent articles of like construction.

After the completion of the above, the dry weight of each of the example absorbent articles was determined. Examples were dried in an oven with an air atmosphere at temperatures that would not degrade the samples (about 4 hrs at 50° C.). At least two weighings at different times with less than a 1% by weight difference determined that the example absorbent articles were dry. The dried example absorbent articles were weighed and the weights recorded as M.

Calculations:

Water absorption with drip after 60 seconds for each test=

$$[(M1-M)/M](100)$$

The water absorption with drip was the average of the 9 tests (3 samples of each example absorbent article tested 3 times.)

Test Method II: Washing Machine "Apparent" Durability

Scope:

To determine the "apparent" durability of stitchbonded absorbent articles of the invention to the agitation experienced in commercially available washing machines.

Equipment:

1. Washing Machine: a commercially available top load washing machine (known under the trade designation "Lady Kenmore Heavy Duty Plus") from Sears, Roebuck & Co.

2. Thermometer: 100° C. maximum with 1° C. graduations.

3. Detergent: a commercially available detergent (known under the trade designation "Tide") from Proctor & Gamble Company.

4. 14 plain (100% cotton) towels, each 76.2 cm×91.4 cm, with a weight of about 1.82 kg each (dry).

5. "Go/no go" samples with varying levels of wear (durability indication.)

Example Size:

15.24 cm×20.3 cm.

Test Conditions:

1. The washing machine was set to the following washing cycle options:

Cotton Sturdy/35 minutes total washing cycle
Hot Wash/Temperature of water 60±5° C.
Warm Rinse Procedure:

1. The 14 plain towels and 10 example absorbent articles of the invention were put into the washing machine.

2. 90 gms of detergent were put into the washing machine.

3. The washing machine was set at the washing machine cycle options as specified above and started.

5. The water temperature was checked to be sure it was 60°±5° C.

6. At the end of the wash cycle the example absorbent articles of the invention were evaluated and compared with unwashed examples noting any variations such as:
color
linting
dimensional changes
wearing (i.e. tearing, delamination, abrasions)
general appearance The washed examples were graded from 1 (=BAD) to 5(=EXCELLENT) according to the scale described below. Since this was subjective and sample dependent, a grading board (board with samples of various grades) was used to minimize operator variability.

7. The example absorbent articles were then rewashed.

8. Retains of the wipes after a particular wash can be done (typically 2 samples are retained after every other wash.)

Typical Grading Scale:

1. BAD—Example absorbent article has fallen apart into pieces or has become severely torn at the edges.

2. POOR—Example absorbent article was falling apart and losing its shape and color. In addition the article was moderately torn at the edges.

3. FAIR—Article lost some shape and color and had begun to fray at the edges.

4. GOOD—Article had almost no discernible loss in shape and color and almost no wear at the edges.

5. EXCELLENT—Article exhibited no obvious change in color, shape and physical appearance.

On an acceptable/not acceptable scale a minimum Grade of 3 is required for acceptance.

Test Method III: Tensile Strength

A modified grab (tensile) test was performed in general accordance with ASTM D 1682-64. In this test, only a part of the width of the specimen is gripped in the clamps. Lateral slits are made are made in the specimen to sever all yarns bordering the portion whose strength is to be tested, reducing to a practical minimum the "fabric assistance" inherent in the grab method. (Section 20 of the standard.) Specimen size used was 100 mm×200 mm. A constant-rate-of-traverse tensile testing machine (known under the trade designation "Sintech") was used, using a machine speed of 305±10 mm per minute. The peak load before break, in Kg, was recorded as the tensile strength of the specimen.

EXAMPLES

In the following Examples, all parts and percentages are by weight unless otherwise specified. In Tables 1-3 the following definitions apply: "395" and "399" refer to the ethylene/vinyl acetate adhesive bonded cellulosic pulp fiber batts known under the trade designation "Airtex", from James River Corporation;

"AM"=absorbent material;
"GA"=stitch gauge (needles per 10 cm, cross direction);
"SD"=stitch density (stitches per 10 cm, machine direction);
"YT"=stitching yarn type;
"PE"=polyester;
"PP"=polypropylene;
"C"=cotton;
"ST"=stitch type;
"PS"=plain stitch;
"TS"=tricot stitch;
"CS"=chain stitch;
"WC"=wash cycles;
"MD"=machine direction;
"therm"=thermobonded material available form Weyerhaeuser Company, Tacoma, Wash., described in U.S. Pat. No. 4,882,213;

and I, II, and III refer to the Test Methods described above.

Eleven Examples within the invention and four controls were made for evaluation. The composition and construction of Examples 1-11 and Controls A-D are presented in Table 1.

TABLE 1

Example Constructions

| Example | AM | # AM | GA | YT | SD | ST |
|---|---|---|---|---|---|---|
| 1 | 395 | 2 | 20 | PE/PP | 30 | PS |
| 2 | 395 | 2 | 20 | C/PP | 30 | PS |
| 3 | 399 | 2 | 20 | C/PP | 30 | PS |
| 4 | 399 | 2 | 20 | PE/PP | 30 | PS |
| 5 | 399 | 2 | 20 | PE/PP | 20 | PS |
| 6 | 395 | 2 | 20 | PE/PP | 20 | PS |
| 7 | 395 | 2 | 40 | PE/PP | 20 | TS |
| 8 | 395 | 2 | 40 | PE/PP | 30 | TS |
| 9 | 395 | 2 | 40 | PE/PP | 30 | CS |
| 10 | 395 | 2 | 13.3 | PE/PP | 30 | PS |
| 11* | 399 | 1 | 13.3 | PE/PP | 30 | PS |
| Control A* | 399 | 1 | — | — | — | — |
| Control B | 399 | 2 | — | — | — | — |
| Control C | 395 | 2 | — | — | — | — |
| Control D | therm | 1 | — | — | — | — |

*Example 11 had construction illustrated in FIG. 4, with layers 42 being 100% viscose rayon, layer 44 being cellulosic pulp fiber batt (trade designation "Airtex 399"). Control A had similar construction but was not stitchbonded.

Table 2 presents data for "apparent" durability, or how stitchbonded articles of the invention appeared after washing (Controls were not subject to washing machine tests as they would disintegrate).

TABLE 2

Washing Machine "Apparent" Durability
Test Method II, number of WCs

| Example | 1 | 3 | 5 | 7 | 9 | 11 | 13 | 15 | 17 | 19 |
|---|---|---|---|---|---|---|---|---|---|---|
| 1 | 5 | 5 | 5 | 4 | 4 | 4 | 4 | 3 | 3 | 3 |
| 2 | 4 | 4 | 4 | 4 | 3 | 3 | 3 | 3 | 3 | — |
| 3 | 4 | 3 | 3 | 3 | 3 | 2 | 2 | 1 | 1 | — |
| 4 | 4 | 4 | 4 | 3 | 3 | 2 | 2 | 2 | 2 | — |
| 5 | 4 | 3 | 3 | 3 | 2 | 2 | 1 | 1 | — | — |
| 6 | 4 | 4 | 4 | 4 | 4 | 3 | 3 | 3 | — | — |
| 7 | 5 | 5 | 5 | 5 | 5 | 5 | 4 | 4 | 4 | 3 |
| 8 | 5 | 5 | 4 | 4 | 4 | 4 | 4 | 4 | 4 | 4 |
| 9 | 5 | 5 | 5 | 5 | 4 | 4 | 4 | 4 | 4 | 4 |
| 10 | 4 | 4 | 4 | 4 | 4 | 4 | 3 | 3 | 3 | 3 |
| 11 | 3 | 2 | — | — | — | — | — | — | — | — |

Table 3 presents results of test methods I and III for Examples 1-11 and Control Examples A-D.

TABLE 3

Water Absorbency and Tensile Strength

| | Test Method | | | | |
|---|---|---|---|---|---|
| | I (Water Abs with drip) | III (Tensile Strength) MD, after WCs, (Kg)* | | | |
| Example | (%) | 0 | 3 | 7 | 19 |
| 1 | 540 | 8.01 | 7.22 | 6.67 | 6.72 |
| 2 | 477 | 9.72 | 11.0 | 10.2 | — |
| 3 | 522 | — | — | — | — |
| 4 | 600 | 8.81 | — | — | — |
| 5 | 656 | 9.85 | 9.17 | — | — |
| 6 | 567 | 10.9 | 8.54 | 8.26 | — |
| 7 | 486 | 17.4 | — | — | — |
| 8 | 420 | 14.5 | 16.8 | 16.6 | — |
| 9 | 440 | 18.0 | — | — | — |
| 10 | 598 | 4.77 | 4.86 | 5.22 | — |
| 11 | 708 | 15.6 | — | — | — |
| Control A | — | 7.95 | — | — | — |
| Control B | — | 1.14 | — | — | — |
| Control C | 837 | 2.21 | — | — | — |
| Control D | 669 | 7.0 | 3.15 | 3.19 | 3.32 |

*Measured in accordance with ASTM 1682-64 (1975)

ANALYSIS OF TEST RESULTS

From the data of Tables 1-3 it may be seen that although Examples 7-9 were the most durable in both the "apparent" and tensile durability tests, they were not as absorbent as some of the other Examples. Examples 1 and 11 appeared to provide the best balance of absorbency and strength.

A comparison can be made between the stitched and unstitched versions of articles of the invention to determine the percent increase in durability and the percent decrease in absorbency after stitchbonding. Comparison of the average tensile strength of all stitchbonded Examples having 2 layers of the cellulosic pulp fiber batt known under the trade designation "Airtex" 395, with an unstitched version (Control C) shows an average of 570 percent increase in tensile strength, but only a 20 percent decrease in absorbency. The same comparison can be made with the article of Control D, a thermobonded article. An average increase of 375 percent in tensile strength, with only a 4.5 percent loss of absorbency was seen. It was highly unexpected that such large increases in tensile strength could be achieved with such small decreases in absorbency.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method of manufacturing a stitchbonded absorbent article wherein the method comprises forming a stitchbonded fabric comprised of cellulosic pulp fibers and adhesive, said fabric having a stitch density ranging from about 15 to about 35 st/10 cm, and stitch gauge ranging from about 10 to about 40, using a stitching yarn comprising first and second fibers of different heat stability, and thereafter heating the stitchbonded fabric for a time and at a temperature sufficient to at least partially melt the first fiber but insufficient to melt the second fiber, thereby melt-bonding at least a portion of the first and second fibers together along points of mutual contact while melt-bonding at least a portion of the first fiber to the outer surfaces of the article.

2. The method of claim 1 wherein the heating step comprises contacting the stitchbonded fabric with the cylindrical exterior surface of at least one perforated or screen drum, the stitchbonded fabric and perforated or screen drums having heated gas passed therethrough via a reduction in pressure on the drum internal volume, and wherein the time of contact of the fabric with the drum external surface ranges from about 15 to about 25 seconds at a temperature of the heated air ranging from about 200 to about 210° C.

3. A method of manufacturing a stitchbonded absorbent article wherein the method comprises forming a stitchbonded fabric comprised of first and second layers, said first layer comprising a nonwoven batt consisting essentially of cellulosic pulp fibers bonded together by an adhesive binder, said second layer comprising materials selected from the group consisting of
  i) a second nonwoven batt consisting essentially of cellulosic pulp fibers bonded together by an adhesive binder, wherein the second nonwoven batt consisting essentially of nonwoven cellulosic pulp fiber being the same or different than the first batt, and
  ii) a woven, nonwoven, or knitted layer of materials selected from the group consisting of viscose rayon, cotton, non-polyolefin synthetic fibers, and mixtures thereof,
wherein the first and second layers are mechanically held together by stitches of yarn, said fabric having a stitch density ranging from about 15 to about 35 st/10 cm, and stitch gauge ranging from about 10 to about 40, using a stitching yarn comprising first and second fibers of different heat stability, and thereafter heating the stitchbonded fabric for a time and at a temperature sufficient to at least partially melt the first fiber but insufficient to melt the second fiber, thereby melt-bonding at least a portion of the first and second fibers together along points of mutual contact while melt-bonding at least a portion of the first fiber to the outer surfaces of the article.

4. The method of claim 3 wherein the heating step comprises contacting the stitchbonded fabric with the cylindrical exterior surface of at least one perforated or screen drum, the stitchbonded fabric and perforated or screen drums having heated gas passed therethrough via a reduction in pressure on the drum internal volume, and wherein the time of contact of the fabric with the drum external surface ranges from about 15 to about 25 seconds at a temperature of the heated air ranging from about 200° to about 210° C.

* * * * *

UNITED STATES PATENT AND TRADEMARK OFFICE
CERTIFICATE OF CORRECTION

PATENT NO.: 5,368,668

DATED: November 29, 1994

INVENTOR(S): Tochacek et al.

It is certified that error appears in the above-identified patent and that said Letters Patent is hereby corrected as shown below:

Col. 9, line 17, " i " should be -- 1 --.

Signed and Sealed this

Twenty-eighth Day of November 1995

Attest:

Attesting Officer

BRUCE LEHMAN

Commissioner of Patents and Trademarks